US011723602B2

(12) United States Patent
Chahine et al.

(10) Patent No.: US 11,723,602 B2
(45) Date of Patent: Aug. 15, 2023

(54) SMART SCALE WITH PLURALITY OF SENSORS

(71) Applicant: MYANT INC., Toronto (CA)

(72) Inventors: Tony Chahine, Toronto (CA); Steve Aitken, Toronto (CA); Adrian Straka, Toronto (CA); Milad Alizadeh-Meghrazi, Toronto (CA); Abdul Javaid, Toronto (CA)

( * ) Notice: Subject to any disclaimer, the term of this patent is extended or adjusted under 35 U.S.C. 154(b) by 251 days.

(21) Appl. No.: 16/959,831

(22) PCT Filed: Dec. 21, 2018

(86) PCT No.: PCT/CA2018/051655
§ 371 (c)(1),
(2) Date: Jul. 2, 2020

(87) PCT Pub. No.: WO2019/134032
PCT Pub. Date: Jul. 11, 2019

(65) Prior Publication Data
US 2021/0361239 A1 Nov. 25, 2021

Related U.S. Application Data

(60) Provisional application No. 62/614,368, filed on Jan. 6, 2018.

(51) Int. Cl.
*A61B 5/00* (2006.01)
*A61B 5/318* (2021.01)
(Continued)

(52) U.S. Cl.
CPC .......... *A61B 5/6892* (2013.01); *A61B 5/0205* (2013.01); *A61B 5/053* (2013.01);
(Continued)

(58) Field of Classification Search
None
See application file for complete search history.

(56) References Cited

U.S. PATENT DOCUMENTS

| 2001/0013855 A1* | 8/2001 | Fricker | G06F 3/045 |
| | | | 345/156 |
| 2005/0113712 A1* | 5/2005 | Petrucelli | G01G 19/50 |
| | | | 324/692 |

(Continued)

OTHER PUBLICATIONS

Cheng et al., "Smart-surface: Large scale textile pressure sensors arrays for activity recognition", Elsevier, Sep. 9, 2015.

(Continued)

*Primary Examiner* — Unsu Jung
*Assistant Examiner* — James Moss
(74) *Attorney, Agent, or Firm* — Norton Rose Fulbright Canada LLP

(57) ABSTRACT

A multi-functional health monitoring mat which enables the measurement of—but not limited to the following parameters: Weight, Plantar pressure, Bio-impedance for body composition, and Cardiovascular based measurements, such as: Electrocardiogram (ECG), Ballistocardiogram (BCG) from which additional health indicating analytics can be further extracted. The mat will be comprised of 3 separate layers: (1) A Bottom Layer, used for weight measurement, comprising force measurement sensors (2) A Middle Layer, used for pressure measurement, comprising pressure sensors in a matrix, and (3) A Top Layer, used for bio-impedance measurement, comprising conductive sensors, distributed throughout the top layer, enabling random orientation of the feet. In addition, there will be an electronic sub-system to enable communication of data and information from the bath mat to a mobile application. Measurements taken from the mat are transmitted to a software application on a mobile phone and data is used to provide feedback to the user.

9 Claims, 10 Drawing Sheets

(51) Int. Cl.
*A61B 5/0205* (2006.01)
*A61B 5/053* (2021.01)
*A61B 5/103* (2006.01)
*G01G 19/44* (2006.01)

(52) U.S. Cl.
CPC ............ *A61B 5/1038* (2013.01); *A61B 5/318* (2021.01); *A61B 5/6804* (2013.01); *G01G 19/44* (2013.01); *A61B 2562/0247* (2013.01); *A61B 2562/0252* (2013.01); *A61B 2562/046* (2013.01); *A61B 2562/06* (2013.01)

(56) References Cited

U.S. PATENT DOCUMENTS

| | | | | |
|---|---|---|---|---|
| 2014/0090489 | A1* | 4/2014 | Taylor | G01L 1/142 |
| | | | | 73/862.626 |
| 2015/0168205 | A1* | 6/2015 | Lee | G01G 21/28 |
| | | | | 177/1 |
| 2015/0201884 | A1* | 7/2015 | Ashokan | A61B 5/6898 |
| | | | | 702/19 |
| 2016/0349104 | A1* | 12/2016 | Yuen | A61B 5/0537 |
| 2017/0061224 | A1* | 3/2017 | Moliner | G06V 40/10 |
| 2017/0146391 | A1* | 5/2017 | Kovacs | G01G 23/007 |
| 2017/0188963 | A1* | 7/2017 | Banet | A61B 5/0205 |
| 2017/0354372 | A1* | 12/2017 | Varadan | A61B 5/282 |

OTHER PUBLICATIONS

Canadian Intellectual Property Office (CIPO), International Search Report and Written Opinion dated May 6, 2019 for PCT/CA2018/051655.

* cited by examiner

SMART SCALE WITH PLURALITY OF SENSORS

CROSS REFERENCE TO RELATED APPLICATIONS

This application claims priority from U.S. provisional patent application No. 62/614,368, filed on Jan. 6, 2018; the entire contents of which are hereby incorporated by reference herein.

TECHNICAL FIELD

The present invention relates in general to a multi-functional health monitoring mat.

BACKGROUND

Recent years have seen a rising trend in terms of wearable products available for health and fitness monitoring. It is not hard to visualize a time in near future when most of these sensors will be embedded in our living environment, thus enabling to gather rich information about our physiological and mental health. Capturing and aggregating this information on continuous basis will not only help improve the way care is delivered today but will also shift the emphasis on pro-active care and managing a healthy lifestyle.

The purpose of the smart mat is to capture information related to health features, such as, plantar pressure and body composition every day. Integrated with and powered by a mobile software app, the user will be given continuous feedback about his weight and other parameters to stay on course for their chosen fitness goals. At the same time, plantar pressure measurements, though dependent on specific application, can help in identifying balance related disorders and also in recovery and rehabilitation phases after injury or accident.

Many studies have shown that monitoring weight on a regular basis helps in achieving weight loss goals more swiftly as compared to weighing yourself once a week. At the same time, body composition can provide further insights into fat content and help in choosing the right fitness plan and managing diet accordingly. Combined with data from other wearable electronics products, like smart watches and smart garments, the information can also help other app developers and healthcare providers in improving sleep and stress levels during the day. At the same time, the secondary outcomes from the project, if required at a later stage, will involve estimation of parameters related to cardiac health, thus broadening the scope and use of such a mat in various settings.

Current state of the art inventions are digital bathroom scales, which incorporate health information such as body mass index (BMI) measurement systems into rigid weight scales. These digital bathroom scales have metallic plate sensors on the left and right side of the scale, upon which each foot is placed and the data being collected. With the value of the data becoming more useful and important only if collected on a regular basis, the current solutions are lacking if the user experience is not simple and automatic. Thus it is readily apparent that a significant drawback of these digital bathroom scales is that they require the user to consciously remember to step on the weigh scale regularly, and place each foot carefully on the left and right sensor pads.

SUMMARY

It is an object of the present invention to provide a mat to obviate or mitigate at least one of the above presented disadvantages.

Thus, with the limitations of prior art stated, provided is an apparatus to monitor health indicators from the feet in a form factor that the user will regularly place his or her feet upon every day, such as a bathroom mat located in front a bathroom mirror. The additional benefit of the bathroom mat is that the user will be standing on the mat while doing other daily grooming habits, such as brushing teeth or combing hair, while inhibiting the need to think about stepping on a scale.

The mat apparatus provides where the measurement can be made where the user's feet can be placed in various orientations on the bath mat in multiple orientations. It is a third object of the invention to describe a system to communicate the health information automatically using a mobile application to record, analyze and display the health data.

A further aspect provided is a mat comprised of separate layers including: a Bottom Layer, used for weight measurement, comprising force measurement sensors; a Middle Layer, used for pressure measurement, comprising pressure sensors in a matrix, and a Top Layer, used for bio-impedance measurement, comprising conductive sensors, distributed throughout the top layer, enabling random orientation of the feet. In addition, there can an electronic sub-system to enable communication of data and information from the bath mat to a mobile application.

A further aspect provided is a monitoring mat for a user comprising: a first layer used for weight measurement, comprising a plurality of force measurement sensors; a second layer, used for pressure measurement, comprising a plurality of pressure sensors in a plurality of pressure locations of a pressure matrix; a third layer, used for bio-impedance measurement, comprising a plurality of conductive sensors configured for direct contact with skin of the user and distributed throughout a surface of the third layer in a plurality of conductive locations of a bio impedance matrix; and a plurality of conductive pathways for each of the layers for connecting the plurality of force measurement sensors, the plurality of pressure sensors and the a plurality of conductive sensors to an electronic controller device for generating and receiving measurement data.

A further aspect is a method of operation for a monitoring mat used by a user comprising the steps of: detecting signals from a plurality of pressure sensors in a pressure matrix layer to determine a first region and a second region of each foot of the user of the mat; correlating the first region and the second region to a first conductive region and a second conductive region containing a plurality of conductive sensors in a conductive matrix layer adjacent to the pressure matrix layer; and activating the plurality of conductive sensors only from conductors located in the first conductive region and the second conductive region in order to collect bio impedance measurement data.

A further aspect provided is a method of operation for a monitoring mat used by a user comprising the steps of: detecting signals from a plurality of pressure sensors in a pressure matrix layer to determine a first region and a second region of each foot of the user of the mat; correlating the first region and the second region to a first conductive region and a second conductive region containing a plurality of conductive sensors in a conductive matrix layer adjacent to the pressure matrix layer; and activating the plurality of conductive sensors only from conductors located in the first conductive region and the second conductive region in order to collect ECG measurement data of the user.

BRIEF DESCRIPTION OF THE DRAWINGS

The non-limiting embodiments may be more fully appreciated by reference to the following detailed description of the non-limiting embodiments when taken in conjunction with the accompanying drawings, by example only, in which.

DETAILED DESCRIPTION

Figure 1A:
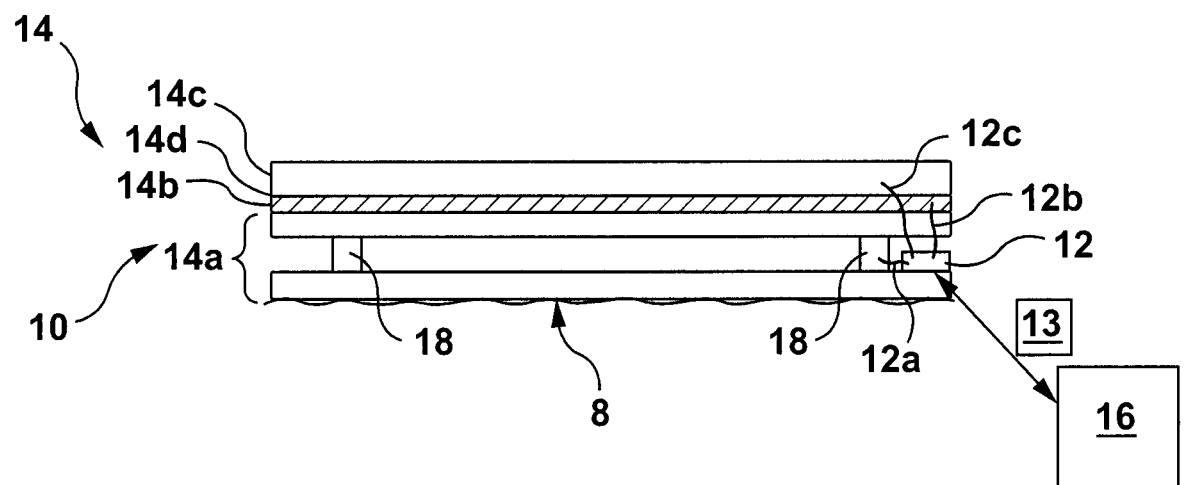
FIG. 1a illustrates a schematic of the mat viewed from the side, comprising multiple layers.
Figure 1B:
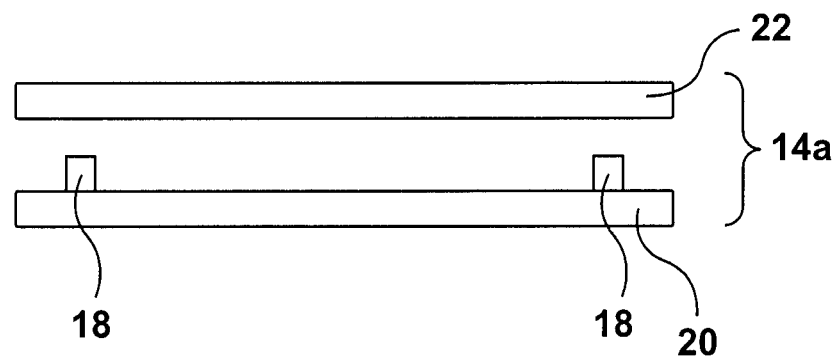
FIG. 1b illustrates a schematic of the bottom layer of the mat, viewed from the side, comprising two hard layers with force measurement sensors (e.g. load cells) between them.

In the following detailed description of exemplary embodiments, reference is made to the accompanying drawings (where like numbers represent like elements), which form a part hereof, and in which is shown by way of illustration specific exemplary embodiments in which a matt apparatus 10 can be practiced. These embodiments are described in sufficient detail to enable those skilled in the art to practice the matt apparatus 10, but other embodiments may be utilized and logical, mechanical, electrical, and other changes may be made without departing from the scope of the present embodiments. The following detailed description is, therefore, not to be taken in a limiting sense, and the scope of the present embodiments is defined only by the appended claims.

In the following description, specific details are set forth to provide a thorough understanding of the embodiments. However, it is understood that the embodiments can be practiced without these specific details. In other instances, well-known structures and techniques known to one of ordinary skill in the art have not been shown in detail in order not to obscure the invention. Referring to the figures, it is possible to see the various major elements constituting the apparatus of the present embodiments.

The present embodiments describe a multi-functional health monitoring mat 10 which provides the measurement of—but not limited to the following parameters: Weight, Plantar pressure, Bio-impedance for body composition, and Cardiovascular based measurements, such as: Electrocardiogram (ECG), Ballistocardiogram (BCG) from which additional health indicating analytics can be extracted from the recorded measurements. Though the primary location of the mat 10 can be in the bathroom—in front of the bathroom sink—it can be easily placed on the kitchen floor in front of the kitchen sink or any other location in the house that is regularly stepped upon. The measurements 13 collected by a controller device 12 as taken from the various layers 14a,14b,14c of the mat 10 can be transmitted by the controller device 12 to a software application on a mobile device (e.g. phone) 16 and measurement data 13 can be used to provide feedback to the user about their health and fitness as extracted/processed using the measurement data 13.

As shown in FIG. 1, the mat apparatus 10 can be comprised of multiple separate layers 14, including such as but not limited to: (1) A first (e.g. Bottom) Layer 14a, used for weight measurement, comprising force measurement sensors 18, (2) A second (e.g. Middle) Layer 14b, used for pressure measurement, comprising pressure sensors 24 in a matrix (see FIG. 1d), and (3) A third (e.g. Top) Layer 14c, used for bio-impedance measurement, comprising conductive sensors 26 (see FIG. 1e), distributed throughout the third layer 14c, facilitating random orientation of the feet when positioned on the third layer 14c of the matt apparatus 10. In addition, there can be the electronic sub-system of the controller device 12 to enable communication of measurement data 13 and information from the bath mat 10 to the mobile device 16 application. It is recognized that each of the layers 14a,b,c have corresponding conductive pathways 12a,12b,12b electrically coupling the respective sensors 18, 24, 26 to the electronics 100 (see FIG. 8) of the controller device 12.

Referring again to FIGS. 1a, 1b, 1c, the purpose of the bottom layer 14a is to provide measurement of weight as the person stands on the mat 10 (e.g. the third layer 14c), such that the first layer 14a is positioned on a corresponding surface 8 (e.g. floor surface of the user's home. Hence, load-cells 18 are used for this purpose as force-resistive or capacitive sensors may not provide an accurate reading for measuring the exact weight of an object. The load-cells 18 can be placed between two solid (i.e. resilient or stiff) layers 20,22; the proposed example arrangement of load-cells 18 can be sandwiched between the two layers 20,22 made of glass or other strong material (see FIG. 1(b)). The measurement data 13 from the load-cells 18 can be combined to obtain the actual weight of the person/object on the mat apparatus 10, as collected from the conductive pathway 12a connecting the load cells 18 to the controller device 12. Other methods for weight measurement can be also being incorporated into this layer 14a, providing they can achieve the accuracy that the measurement requires.

Figure 1C:
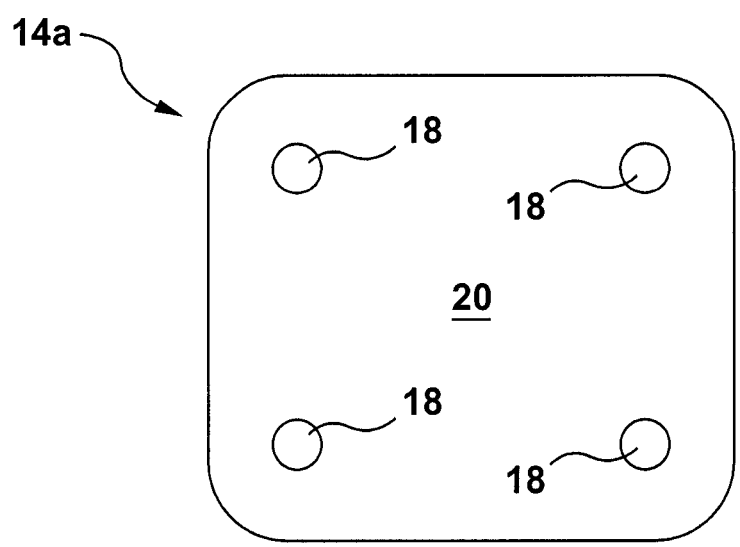
FIG. 1c shows a top view of the bottom layer.

One example of the load cell 18 is a transducer that is used to create an electrical signal (e.g. measurement data 13) whose magnitude is directly proportional to the force being measured (i.e. the weight of a person standing on the matt apparatus 10. The various load cell 18 types can include hydraulic, pneumatic, and strain gauge. For example, one embodiment the load cell 18 is strain gauge load cells. These load cells can be particularly stiff, have desired resonance values, and can tend to have long life cycles in application. Strain gauge load cells 18 work on the principle that the strain gauge (a planar resistor) of the load cell 18 deforms when the material of the load cells deforms appropriately, i.e. due to applied weight of the user of the matt apparatus 10. Deformation of the strain gauge changes its electrical resistance, by an amount that is proportional to the strain. The change in resistance of the strain gauge provides an electrical value change that is calibrated to the load placed on the load cell 18, and therefore produces a weight measurement data 13 that can be calibrated to weight measurement (e.g. in pounds or kilograms). FIG. 1c shows a top view of the layer 20 having a distribution of the load cells 18.

Figure 1D:
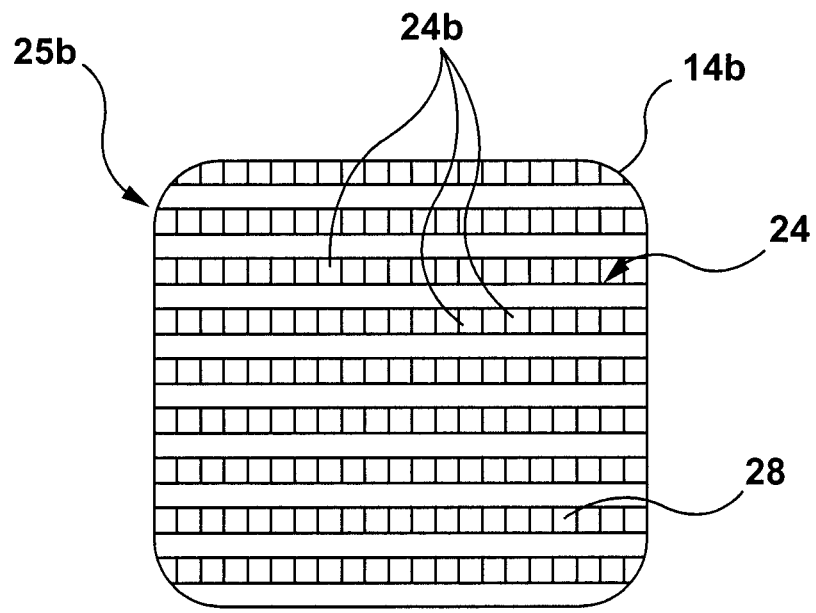
FIG. 1d illustrates a pressure matrix sensor layer (i.e. middle layer), used for plantar pressure measurement.
Figure 3:
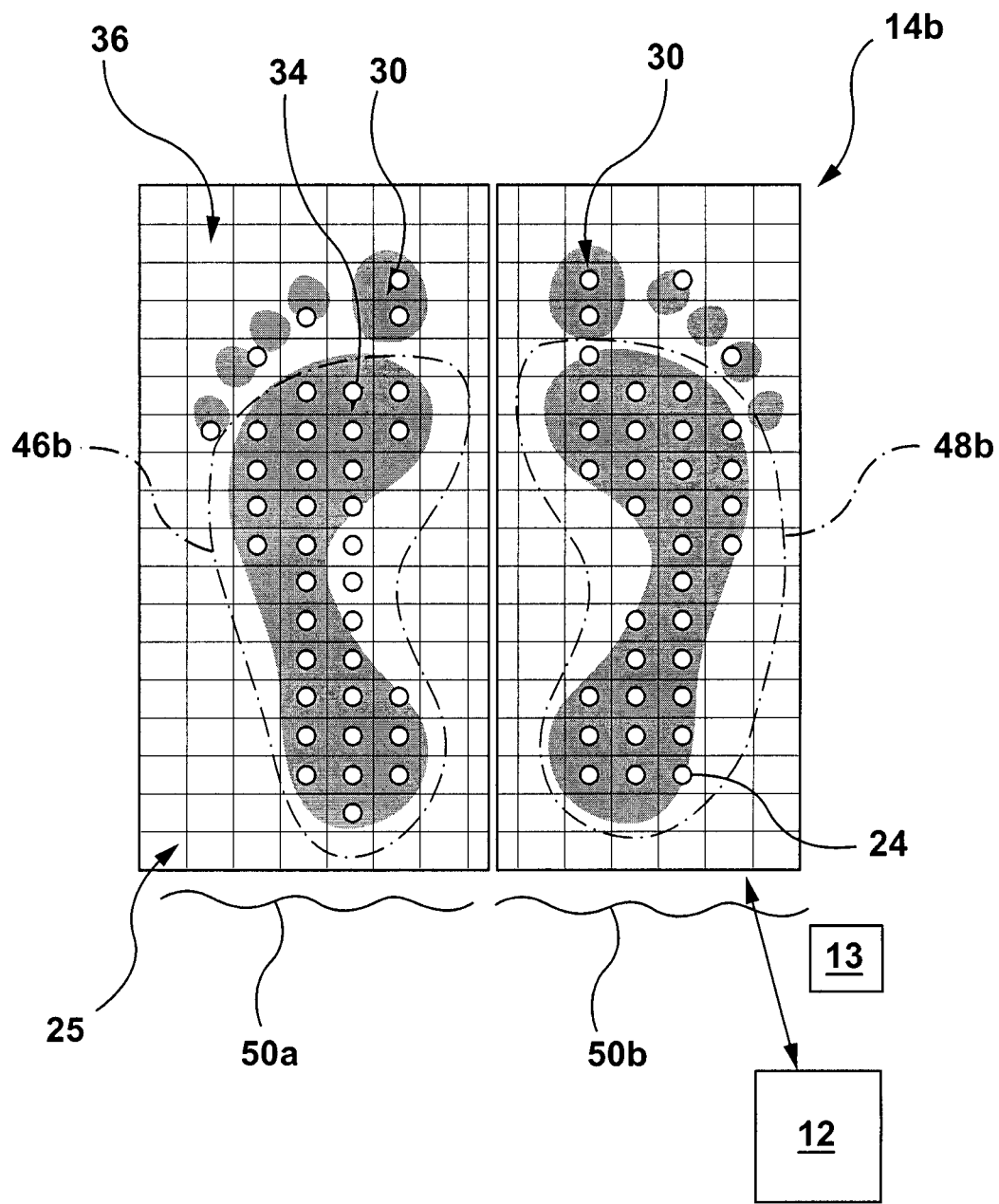
FIG. 3 illustrates detection of footprints on the pressure sensing layer to activate electrodes on the bio-impedance layer.

Referring to FIG. 1d, the second (e.g. middle layer) matrix 25b of pressure sensors 24 can be used to measure plantar pressure (see FIG. 3). The layer 14b can be composed of the pressure matrix sensors 24, e.g. tactile sensors such as piezo-resistive traces, distributed in discrete locations 24b over a surface 28 of the second layer 14b as the matrix 25b (collection of locations 24b) and can be used to record pressure distribution of the contact body (e.g. the soles/toes 30 of the feet of the user as first group 46b and second group 48b representing the overall feet locations on the matrix 25b). The grid like structure of the individual sensors 24 positioned in respective defined locations 24b (e.g. coordinates) of the matrix 25b can be configured to provide a specific spatial resolution of the pressure measurements data 13 (e.g. as a pressure map recording both magnitude and location 24b of each individual pressure sensor 24 measurement) for more accurate and certain applications.

In this embodiment, the measurement data 13 for pressure can made using a force-resistive sensing array sheet, available off the shelf with simple to use Arduino™ boards such as from Adafruit™ Industries. Textile sheets may also be used to replace this printed layer in other embodiments. For example, the individual pressure sensors 24 can be a Force-Sensitive Resistor sold by Adafruit™, as a resistor that changes its resistive value (in ohms Ω) depending on how much its pressed. Accordingly, the controller device 12 has stored in memory 102 (see FIG. 8) a spatial distribution 24b(e.g. relative coordinate locations 24a in the matrix 25b) of each individual pressure sensor 24, such that a corresponding pressure value for each sensor 24 can be identified, e.g. calibrated from 0 to a maximum pressure value. As such, the pressure measurement data 13 from the pressure sensors 24 can be used by the controller device 12 to detect in which locations 34 the user is standing (e.g. detecting a calibrated pressure measurement greater than a rest value (e.g. 0)) as compared to those locations 36 in the pressure map (of the matrix) exhibiting or otherwise maintaining the rest values (e.g. 0), see FIG. 3. Therefore, the controller device 12 can identify by pressure value (e.g. rest or greater than rest) those matrix 25 (e.g. grid) locations 34 in which the user is standing and in those locations 36 in which the user is absent (i.e. not standing).

Figure 1E:
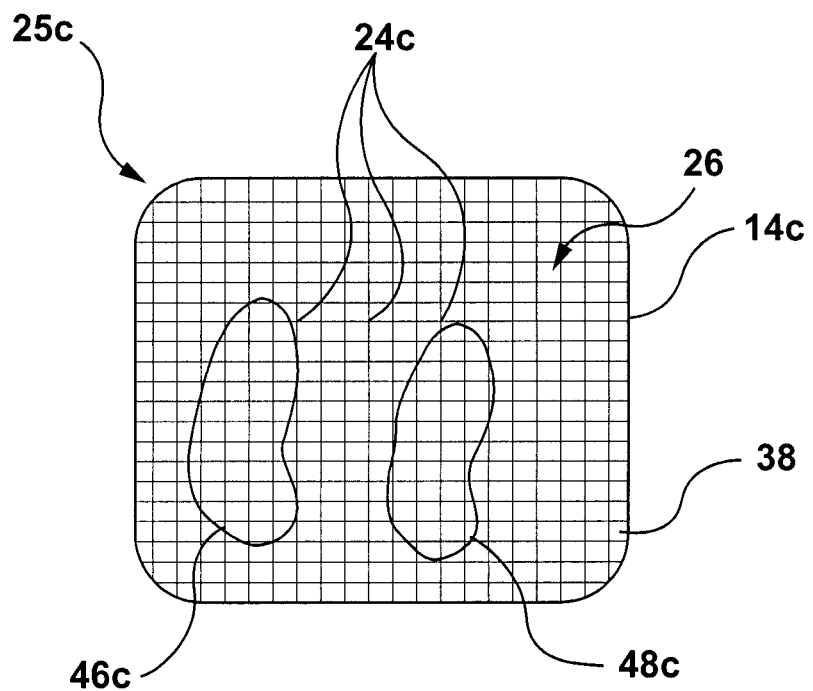
FIG. 1e illustrates a schematic of the top layer, comprising textile based material which will be used as a bio-impedance measure layer in direct contact with feet.

Referring to FIG. 1e, shown is the third layer 14c by example, having a plurality of bio impedance sensors 26 positioned in a matrix 25c of sensors 26 can be used to measure bio impedance values in locations 24c corresponding (or adjacent thereto) to the locations 24b (see FIG. 3). In any event, the locations 24c are correlated with the locations 24b, such that the coordinates in the matrix 25c correspond with the coordinates in the matrix 25b. For example, the locations 24c can overlay or otherwise be congruent (e.g. the same) with the locations 24b. Alternatively, or in addition to, the locations 24c can be offset but otherwise adjacent to the locations 24b, such that the locations 24c are associated individually with the respective locations 24b. The layer 14c can be composed of the bio impedance matrix sensors 26, e.g. electrodes such as but not limited to one or more conductive fibres positioned at each of the individual locations 24c, such that each of the bio impedance sensors 26 can be activated individually/independently with respect to others adjacent in the matrix 25c. Therefore, the bio impedance sensors 26 are distributed in discrete locations 24cb over a surface 38 of the third layer 14c as the matrix 25c (collection of locations 24c) and can be used to record bio impedance of the contact body (e.g. the soles/toes 30 of the feet of the user). The grid like structure of the individual sensors 26 positioned in respective defined locations 2c (e.g. coordinates) of the matrix 25c can be configured to provide a bio impedance measurements data 13 of the user. It is also recognised that the sensors 26 (e.g. actuators) can be used for sensing measurement data 13 other than bio impedance, such as ECG data, etc. It is recognized that the sensors 26 actuators 26 are made of electrically conductive material used to generate and receive electrical current when in direct contact with the skin of the user.

Bioelectrical impedance analysis (BIA) is method performed by the controller device 12 for estimating body composition, and in particular body fat. BIA actually determines the electrical impedance, or opposition to the flow of an electric current through body tissues of the user (e.g. as applied to one sole of the feet using one or more bio impedance sensors 26 selected from the matrix 25c as current signal generating bio impedance sensor(s) 26 adjacent to the sole and as received by the other sole of the feet using one or more bio impedance sensors 26 selected from the matrix 25c as current signal receiving bio impedance sensor(s) 26 adjacent to the other sole), which can then be used to estimate total body water (TBW), which can be used to estimate fat-free body mass and, by difference with body weight, body fat, by the controller device 12, as desired. The impedance of cellular tissue can be modeled as a resistor (representing the extracellular path) in parallel with a resistor and capacitor in series (representing the intracellular path). This can result in a change in impedance versus the frequency used in the measurement data 13 relating to bio impedance readings of the bio impedance sensors 26. The impedance measurement 13 can generally measure from the sole of one foot to the sole of the other foot and can use a group of electrodes 26 (e.g. either two or four electrodes 26). A current on the order of 1-10 µA can be passed between two groups of electrodes 26, a first group 46c adjacent to one foot and a second group 48c adjacent to the other foot, and the voltage is measured by the controller device 12 between the same (for a two electrode configuration) or between the other two electrodes 26, for example. The groups 46c,48c of the electrodes 26 can be selected based on the value readings of the pressure matrix 25b as identified above via the pressure measurement data 13 collected by the controller device 12 by the pressure sensors 24 of the second layer 14b (see FIGS. 1d and 3).

This is possible, as the locations 24c of the bio impedance sensors 26 are correlated with the locations 24b of the pressure sensors 24. For example, the controller device 12 can choose those locations 24b having a pressure measurement 13 above a specified pressure threshold (e.g. greater than a rest/null values, greater than a defined pressure value greater than rest value, and/or one or more locations exhibiting a relative maximum pressure value as compared to other locations 24b of the group locations 34). For example, the controller device 12 could pick a first group of locations 24b having the largest relative pressure measurements of all locations 24b for one foot as the generating foot and then select a second group of locations 24b having the largest relative pressure measurements of all locations 24b for the other foot as the receiving foot. Further, the overall matrix 25b can be separated into separate "foot" regions 50a,b (e.g. halves), in order to define one foot general location from the other foot general location, see FIG. 3. Once the controller device 12 has the first and second group locations of the matrix 25b, the controller device can map those locations onto the locations 24c of the matrix 25c using the correspondence information between the locations 24b, 24c, in order to identify the optimum of the locations 24c from which to select the adjacent bio impedance sensors 26 (e.g. first group 46c and second group 48c). Once selected, one or more of the respective bio impedance sensors 26 in the first group 46c can be activated (sequentially and/or simultaneously) and then one or more of the respective bio impedance sensors 26 in the second group 48c can be used to record (sequentially and/or simultaneously) the resultant current transmitted through the body of the user from the one foot to the other foot.

Figure 5:
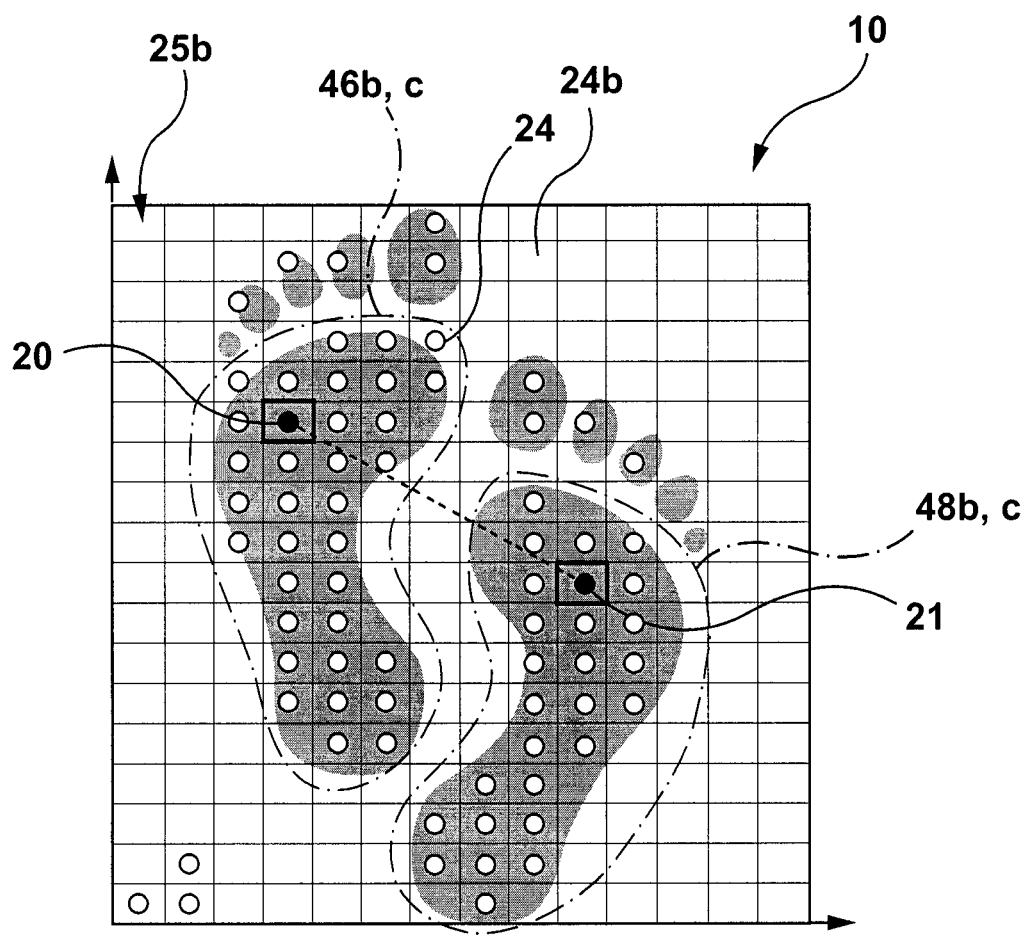
FIG. 5 illustrates the activation of different pressure sensors on the grid.

The purpose of the third layer 14c/bio-impedance and ECG (electrocardiogram) sensors 26 (noting that the current emitting/receiving electrodes 26 can be used for a variety of purposes, as configured for use by the controller device 12) can be to provide a soft comfortable surface to stand on along with the ability to do bio-impedance based body composition using (e.g. textile) electrodes 26 comprised as a series of interlaced fibre groups at each of the locations 26c of the matrix 25c. However, other bio impedance sensor 26 types can be used, for example gel type electrodes. As shown in FIG. 1 (e), the bio-impedance electrodes 26 are arranged in a grid like structure 25c similar to the pressure layer 14b just below it. The size and position of grid elements/locations 24c (e.g. squares as in FIG. 1(e)) on the third layer 14c can correspond (e.g. exactly the same) to the position of the pressures sensor 24 grid 25b below the layer 14c. It is recognized that the layers 14b,14c can be adjacent to one another or can have an optional intervening layer 14d there between (see FIG. 1a). It is also recognised that the third layer 14c is preferably the layer 14 closest to the user, e.g. in direct contact with the skin of the user, in order to provide for appropriate current measurement related to bio impedance measurement data 13. For example, as shown in FIG. 5, the identified maximum pressure location 46d and 48d by the controller device 212 using the pressure matrix 25b can be correlated to the corresponding locations 24c of the matrix 25c and thus those bio impedance sensors 26 located at those maximum pressure locations 46d, 48d could be used in the bio impedance measurement data 13 collection process, recognizing that bio impedance (or ECG for that matter) is best measured when appropriate levels of direct contact between the sensor(S) 26 and the shin is achieved. It is assumed that at maximum pressure location(s) 4d,48d, as identified, would also be where the best skin contact with the sensors 26 can be realized/expected.

As described above, as the person stands on the mat 10, the pressure sensors 24 can sense the location of the two feet. The specific grid points 26c on the top layer 14c (bio-impedance layer) of the mat 10 can then be activated using the pressure information obtained from the layer 14b below it, thus, inhibiting the need to stand on specific points on the mat 10 in order to facilitate the sensor electrode 26 usage (e.g. for bio impedance, for ECG, etc.). The individual sensors 24,26 on both layers 14b,14c (e.g. bio-impedance and pressure) are shown as of square shape in FIGS. 1d, 1e. However, these individual sensors 24,26 can take any geometrical shape as long as the both layers 14b,14c have similar (e.g. the same number) of sensors 24,26 and are associated (e.g. aligned or otherwise offset/adjacent) on the horizontal and vertical axes of the matrices 25b,25c. It is recognized that the number of sensors 24 can be the same as the number of sensors 26. Alternatively, it is recognized that the number of sensors 24 can be less than the number of sensors 26. Alternatively, it is recognized that the number of sensors 26 can be less than the number of sensors 24.

In some embodiments, the top layer 14c can be made removable from the rest of the mat 10 for washing and drying in a washing machine. Also, the intermediate layer 14d made of soft material can be placed between the top bio-impedance layer 14c and the layer 14b for the matrix pressure sensor array 25b.

In some embodiments, a similar method for measuring bio-impedance using a textile sensor 26 touching each foot can also be used to extract an electrocardiogram (ECG) measurement which can be analyzed for further heart metrics.

Figure 9:
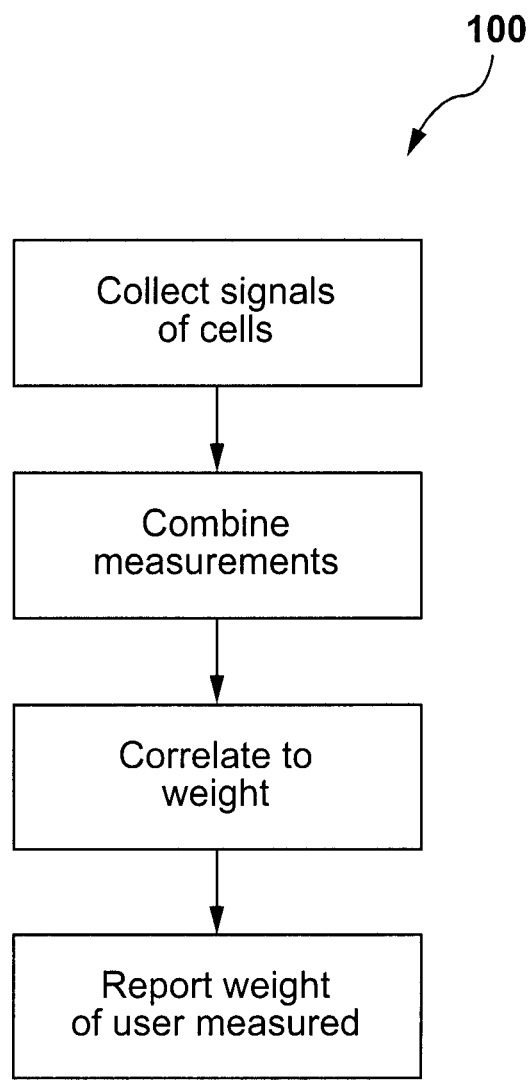
FIG. 9 is an example operation of the controller device of FIG. 1 to determine a weight of a user of the mat of FIG. 1.

A method 100 (see FIG. 9) of operation for the controller device 12 is presented, wherein signals are collected from the conductive pathways 12a connected to each of the load cells 18 (e.g. the weight measurement sensors (e.g. 4-load sensors)) are combined by the controller device 12 from to get an estimate of the total weight of the user.

Figure 7:
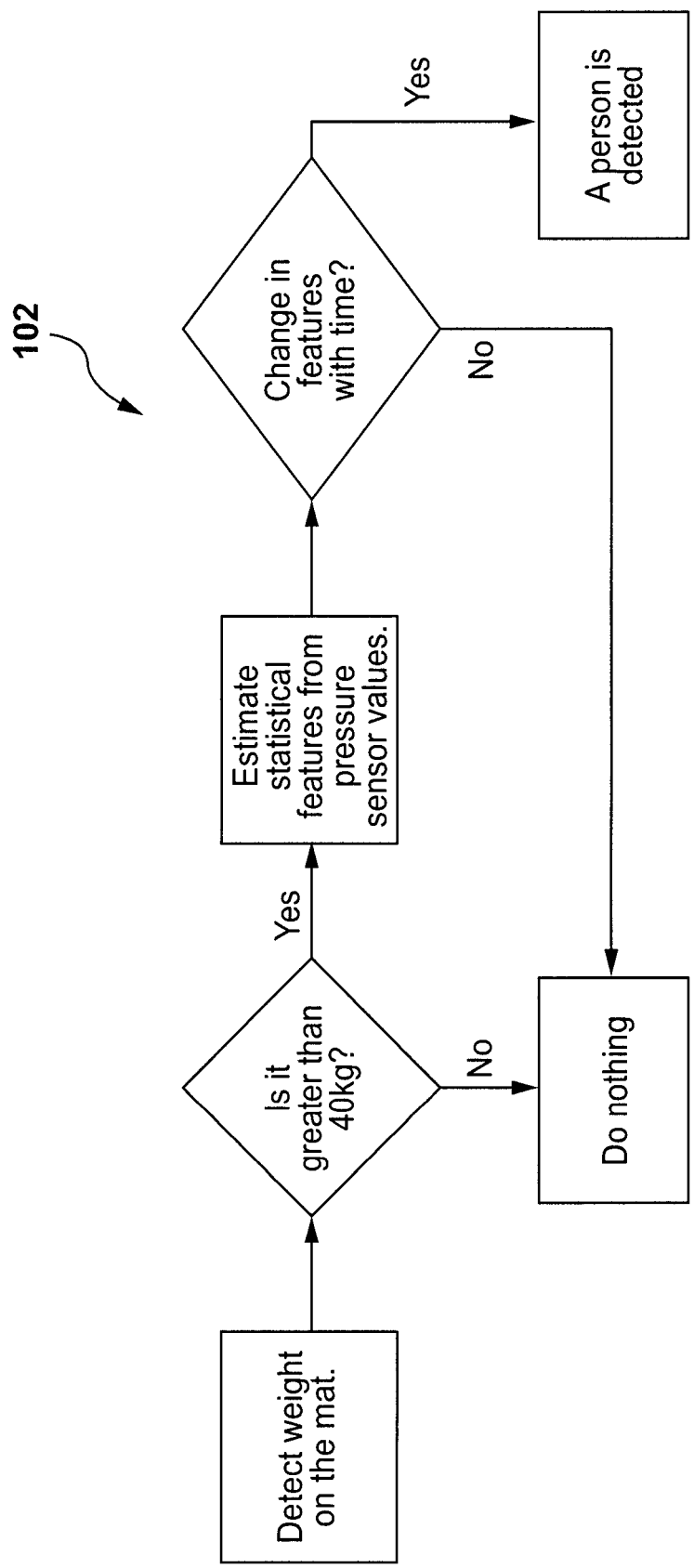
FIG. 7 describes a flowchart for detection of a human being on the mat.

A method 102 (see FIG. 7) of operation for the controller device 12 is presented, wherein the presence of a human is detected on bath mat using ballistocardiography methodology. In this example, once the person presence is detected, then the controller device 12 can proceed to record measurements from any or all of the layers 14a,b,c, as desired. For example, measurements data 13 from layer 14b first can be used to coordinate appropriate measurement data 13 collected from layer 14c second.

Figure 2:
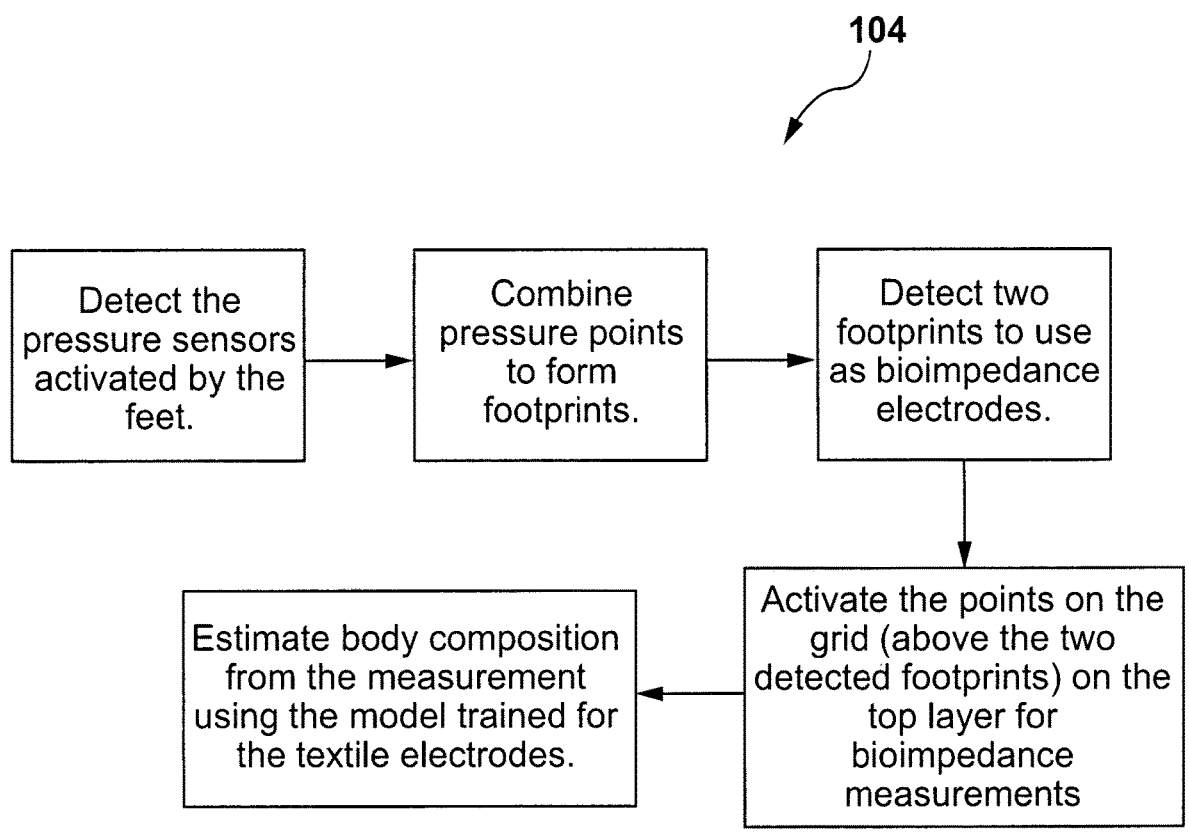
FIG. 2 describes a flowchart and algorithm for automated bio-impedance measurements from the mat.

A method 104 of operation for the controller device 12 is presented, to detect footprints on the bath mat 10 using the pressure sensors 24 and then use these reference locations 46b,c, 48b,c from which to select the bio-impedance electrodes 26 (see FIG. 2). As the person stands on the mat 10, the second layer 14b composed of the pressure sensing matrix grid 25b is used to detect the points 24b on the pressure grid 25b. The number of sensors 24 (points 24b on the grid 25b) are combined to form larger areas 46b,48b to detect each foot print. If two or more activated sensors 24 are next to each other, then they can combined to form the one region 46b, 48b. The patch 46b,48b is then grown by adding each activated sensor 24 which is present on any side 50a,50b of the resultant region.

A method 106 of operation for the controller device 12 is presented, to detect pressure points 24b on the pressure sensor grid layer 14b to detect footprints (e.g. groups 46b, 48b in the two halves 50a,50b of the bathmat 10 as show in FIG. 3. The mat 10 is divided into two layers 14b,14c and two halves 50a,50b. As the person stands on the mat 10 with one foot in each half 50a,b, the pressure sensor 24 detecting (e.g. activated and thus sending a current signal to the controller device 12 via the conduction pathways 12b connecting each of the sensors 24 with the collection interface 94 (see FIG. 8) the footprints in each half 50a,b are detected. For the left foot, the maximum intensity point 24b (say L0) which specified by its location 24b and intensity value in the left grid 50a (as shown in FIG. 3) or left half of the plane is first detected by the controller device 12. If there are points 24b on the grid 25b adjacent to this maximum intensity point 24b, these 24b are combined with L0 24b to form a patch 46b. The patch 46b is then grown to include adjacent points 24b on the grid 25b which are indicating a pressure value (e.g. other than rest/null). In this way, the patch 46b is grown until it encompasses all the pressure sensors 24 on the grid 25b activated by the left foot and which are adjacent to each other. The pressure sensors 24 on the grid 25b which are not adjacent to this newly formed region 46b are not included in the process (see FIG. 4 for an example flow chart of the method 106). A similar process is carried out for the right foot in the right hand plane 50b. For the right foot, the maximum intensity point 24b (say L1) which specified by its location 24b and intensity value in the right grid 50b (as shown in FIG. 3) or right half of the plane is first detected by the controller device 12. If there are points 24b on the grid 25b adjacent to this maximum intensity point 24b, these 24b are combined with L1 24b to form a patch 48b. The patch 48b is then grown to include adjacent points 24b on the grid 25b which are indicating a pressure value (e.g. other than rest/null). In this way, the patch 48b is grown until it encompasses all the pressure sensors 24 on the grid 25b activated by the right foot and which are adjacent to each other. The pressure sensors 24 on the grid 25b which are not adjacent to this newly formed region 48b are not included in the process (see FIG. 4 for an example flow chart of the method 106).

Figure 4:
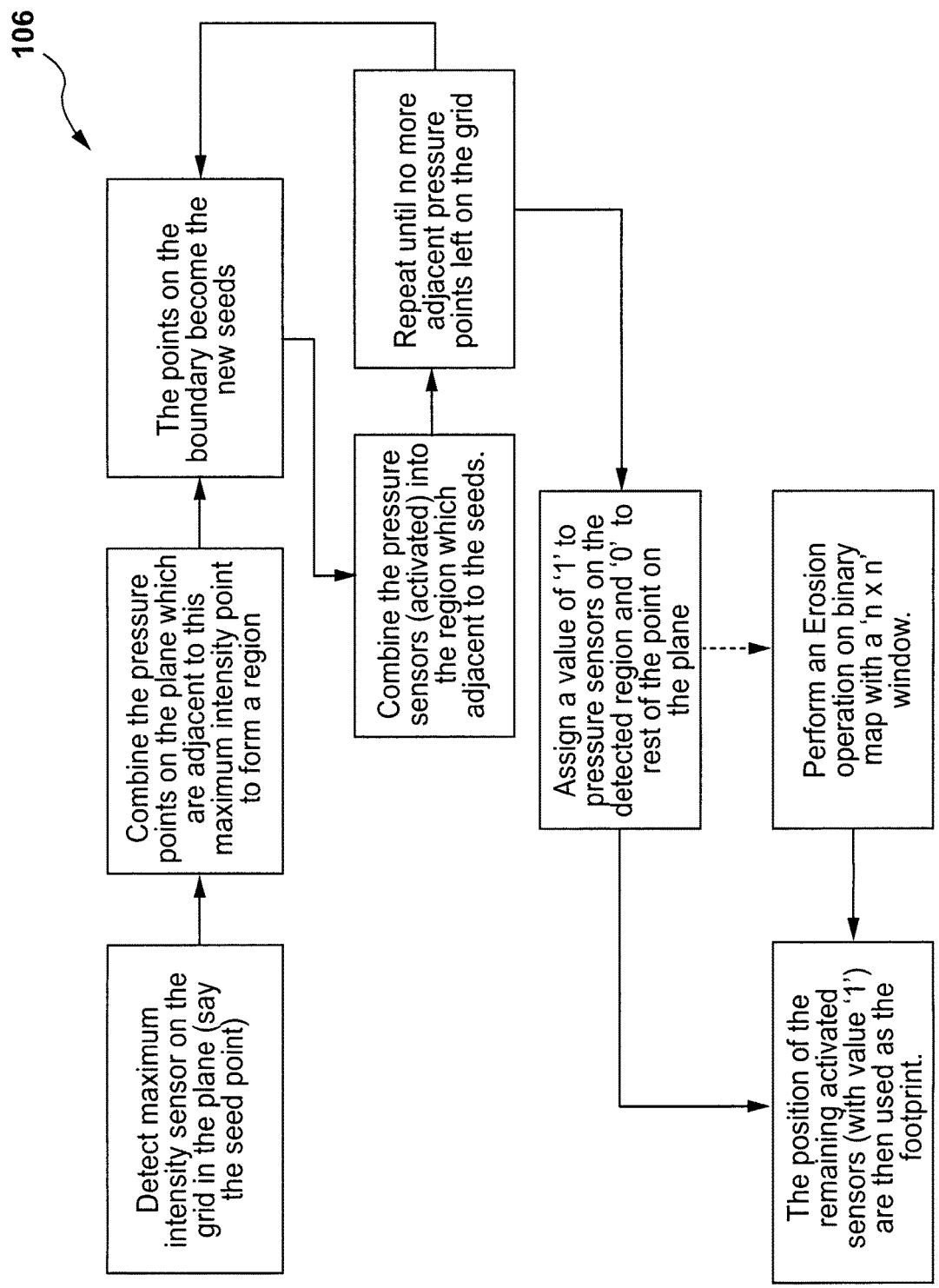
FIG. 4 describes a flowchart for the detection of a footprint on the pressure sensing grid.

In some embodiments where the spatial resolution of the pressure sensors 24 on the grid 25b is concentrated, once the region 46b,48b is detected, it can be followed by an erosion operation with an 'n n' matrix (as shown in FIG. 4) to further refine or shrink the region for detection of footprints. The value of 'n' can be chosen depending upon the spatial resolution of the pressure sensor grid 25b.

In some embodiments, the resultant structure 46b,48b obtained corresponding to the footprint after the above operations can then be compared with a corresponding image (pressure) of the foot to refine the results using a template matching.

Figure 6:
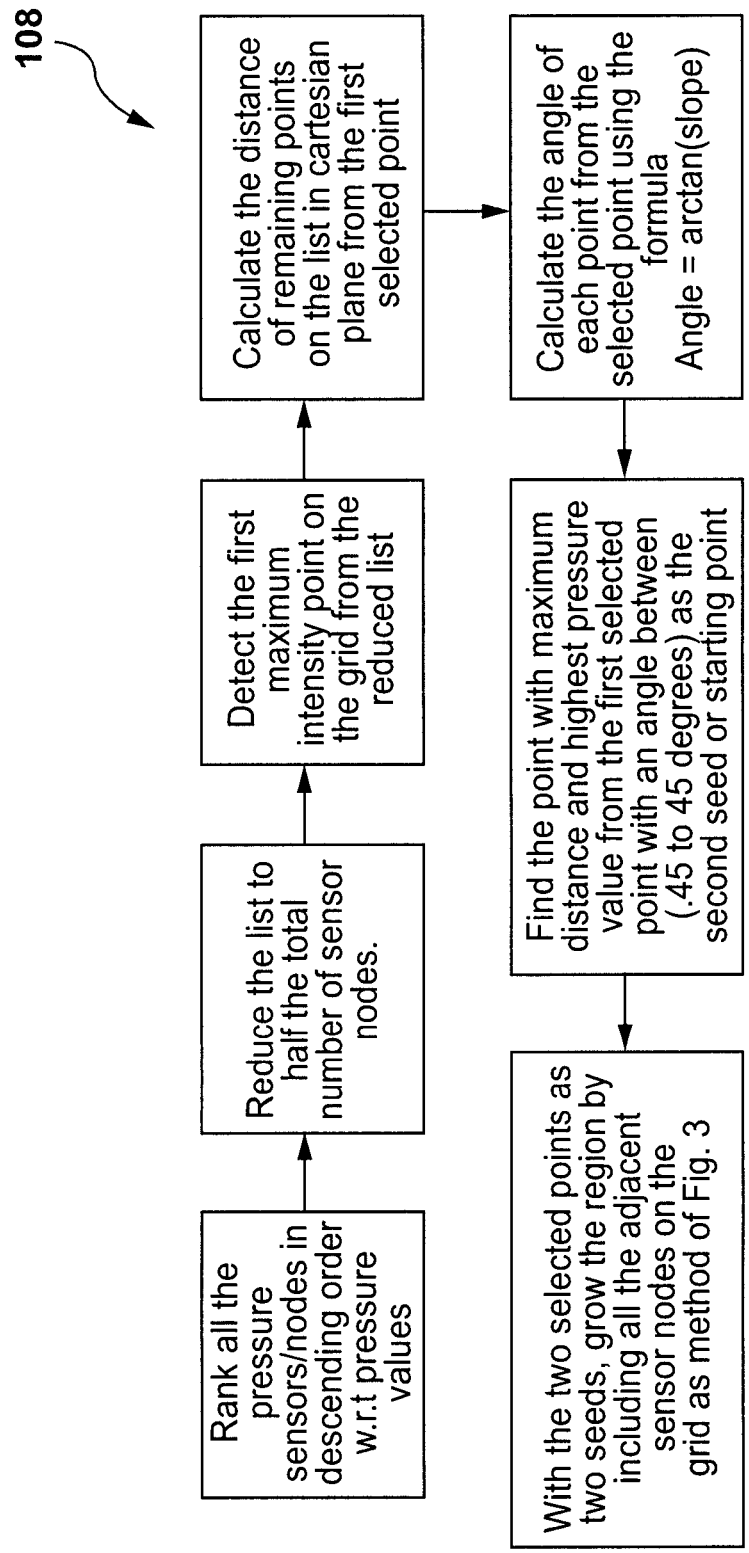
FIG. 6 describes a flowchart for an algorithm to detect regions on the sensor grid corresponding to two footprints.

A threshold based method 108 is presented (see FIG. 6) to detect footprints on the pressure sensing grid 25b with a divider that separates the plane into two halves 50a,b. The pressure sensors 24 which show a value of pressure above a certain threshold are assigned a value of '1' while the remaining points are assigned a value '0'. This is followed by a dilation process on the resultant binary grid 25b values. An image morphology operation such as erosion, dilation, opening, closing or a combination of these can be then be performed on the resultant binary image (pressure grid map) to find the position and location of the points 24b on the grid corresponding to a footprint (e.g. regions 46b,48b).

A method of operation for the controller device 12 is presented to detect footprints (pressures sensors 24 corresponding to a foot as the person stands on it) on a pressure sensor grid 25b without any divider that splits the plane into two halves (see FIG. 5). As the person stands on the mat 10, the pressure sensors 24 and their location 24b is first detected on the grid 25b. The sensors 24 are then ranked in descending order based on the pressure value. The point (sensor) 24b with the highest value is then chosen as the first point (L0) or the seed to grow a region 46b,48b. The second seed is chosen as the next highest pressure sensing node 24b on the grid 25b which is located horizontally/adjacent to the first seed. The direction and more specifically the angle is determined from the coordinates of the sensors/nodes 24b on the grid 25b. See FIG. 6 for more details. Once the two regions 46b,48b are detected, they are refined further using operations as described.

The methods of operation 104,108,108 for the controller device 12 is presented based on methods described previously to detect total pressure and related features on both feet as the subject stands on the mat 10. The grid points 24b detected for both footprints are used to find the number and location of pressure sensors 24 activated/sensing pressure for each foot. The features extracted may include, but not limited to, total pressure obtain by integrating values for pressure sensors 24 in the region 46b,48b corresponding to each foot, statistical features like standard deviation, variance, mean absolute deviation, kurtosis etc., features from frequency domain obtained from a 2-D Fourier Transform of the region 46b,48b corresponding to each foot region shown in FIG. 3 and FIG. 5, and difference of statistical measures between the two feet. In some embodiments, the pressures related features from both feet will be compared to get information related to balance and posture. In some embodiments, the features can be compared for a certain duration of time to get information related to balance and postural sway.

A method of operation 102 for the controller device 12 is presented to detect human presence on the bathmat 10. If the weight on the bathmat 10 exceeds a certain threshold (40 kg), then the controller device 12 identifies it as a subject standing on it. Furthermore, once a person or any object stands or placed on the mat 10, the sensor nodes 24 on the grid 24b which sense pressure are detected and the statistical features like standard deviation and variance of pressure values can be estimated to check for ballistocardiography based movement of human body due to perfusion of blood into vasculature. In case, the statistical features do not show any change, the mat 10 does not detect the object as a living person and no estimation for pressure and bio-impedance based metrics could be carried out (See FIG. 7). Such a method can also stop the mat 10 to perform any calculation if a minor/child is standing on the mat.

In some embodiments, the positions of the sensors 24,26 on the grid 25b,25c are used to choose the two highest force sensors away from each other to form clusters. In some embodiments, plantar pressure sensing using pressure film and textile based sheets provides the capability to assess disorders related to balance and posture, such as muscle tightness and joint problems. In some embodiments, heart rate estimation analysis from ballistocardiography signal is obtained from modifying the load-cell circuit. In some embodiments, the estimation of systolic time intervals and cardiac output in non-clinical settings for patients with heart failure or other cardiovascular diseases are realized.

Figure 8:
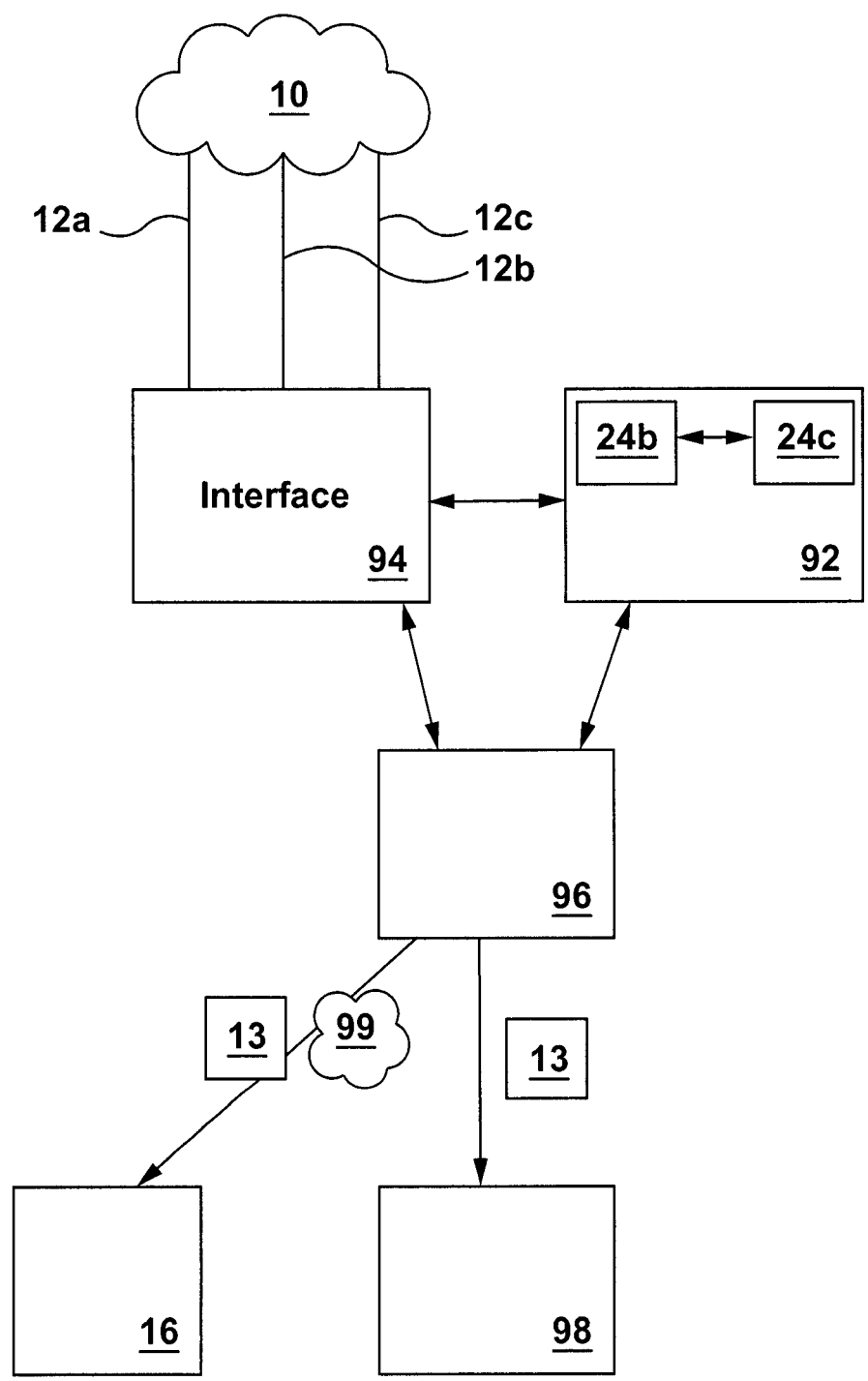
FIG. 8 provide an example controller device of the mat of FIG. 1.

Referring to FIG. 8, the controller device 12 is shown with functional data processing blocks. In certain embodiments, the one or more components 92,94,96 that are set to be executed or run on a computing device (e.g. controller device 12) or otherwise in communication over a network 99 with a mobile electronic device 16. The controller device 12 on which the present embodiments can be operated could be comprised of a CPU processor 96, memory 92 (e.g. Hard Disk Drive, CPU Main Memory and a portion of main memory where the stored system instructions reside and are used to execute by the computer processor 96). Also provided can be a user interface 98 (e.g. display, microphone, speaker, etc.) that can be used by the controller device 12 in order to display measurement data 13 in any processed format to the user, as desired.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The invention claimed is:

1. A monitoring mat for a user comprising:
   a first layer used for weight measurement, comprising a plurality of force measurement sensors;
   a second layer, used for pressure measurement, comprising a plurality of pressure sensors in a plurality of pressure locations of a pressure matrix;
   a third layer, used for bio-impedance measurement, comprising a plurality of conductive sensors configured for direct contact with skin of the user and distributed throughout a surface of the third layer in a plurality of conductive locations of a bio impedance matrix, wherein respective pressure sensors at the plurality of pressure locations are positionally correlated with at least one conductive sensor at the plurality of conductive locations; and
   a plurality of conductive pathways for each of the layers for connecting the plurality of force measurement sensors, the plurality of pressure sensors and the plurality of conductive sensors to an electronic controller device for generating and receiving measurement data, wherein a subset of the plurality of conductive sensors is activated based on pressure measurement data generated by the plurality of pressure sensors.

2. The mat of claim 1, wherein the plurality of force measurement sensors are load-cells placed between a first resilient layer and a second resilient layer of the first layer.

3. The mat of claim 2, wherein the first resilient layer and the second resilient layer are made of glass.

4. The mat of claim 1, wherein the second layer is positioned between the first layer and the third layer.

5. The mat of claim 1, wherein the third layer includes the plurality of conductive sensors as fibre based sensors embedded in a textile based material comprising the third layer.

6. The mat of claim 5, wherein the third layer is removable from the second layer.

7. The mat of claim 1, wherein a number of the plurality of pressure sensors and a number of the plurality of conductive sensors is the same.

8. The mat of claim 1 further comprising an intermediate layer positioned between the third layer and the second layer.

9. The device of claim 1, wherein the plurality of conductive sensors are also used for measuring an electrocardiogram (ECG) measurement.

* * * * *